(12) United States Patent
Makharinsky et al.

(10) Patent No.: US 10,729,902 B1
(45) Date of Patent: *Aug. 4, 2020

(54) INTRASEPTAL MULTI-ELECTRODE CARDIAC PACEMAKER AND METHODS OF USE THEREOF

(71) Applicant: Eagle Point Medical LLC, City of Dover, DE (US)

(72) Inventors: Leonid Makharinsky, Bonassola (IT); Daniel Lev Makharinsky, Chalfont St Giles (GB)

(73) Assignee: Eagle Point Medical LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/826,259

(22) Filed: Mar. 22, 2020

Related U.S. Application Data

(63) Continuation-in-part of application No. 16/221,547, filed on Dec. 16, 2018, which is a
(Continued)

(51) Int. Cl.
*A61N 1/05* (2006.01)
*A61N 1/39* (2006.01)
(Continued)

(52) U.S. Cl.
CPC ............ *A61N 1/059* (2013.01); *A61N 1/3686* (2013.01); *A61N 1/37512* (2017.08); *A61N 1/39622* (2017.08)

(58) Field of Classification Search
CPC ............ A61N 1/36014; A61N 1/36003; A61N 2/002; A61N 2/006; A61N 2/02;
(Continued)

(56) References Cited

U.S. PATENT DOCUMENTS 5,083,564 A 1/1992 Scherlag
5,251,643 A 10/1993 Osypka
(Continued)

OTHER PUBLICATIONS

Huang W et al. A beginner's guide to permanent left bundle branch pacing. Heart Rhythm 2019;16:1791-1796.

*Primary Examiner* — Mark Bockelman
(74) *Attorney, Agent, or Firm* — Boris Leschinsky

(57) ABSTRACT

An intraseptal multi-electrode cardiac pacemaker has a plurality of first individual electrodes implanted at an interventricular septum at varying depths and/or lateral distances from the distal end of a flexible conduit and configured to provide a cardiac pacing therapy by stimulating left bundle branch conduction fibers. A plurality of second individual electrodes may also be implanted in the septum at suitable depths to stimulate conduction fibers of the right bundle branch. After implantation, first and second individual electrodes are interrogated to select a subset of electrodes suitable to deliver the pacing therapy according to a predetermined criterion such as capturing the left ventricle or capturing the right ventricle via normal conduction system of the heart at the lowest voltage level via corresponding bundle branches. A combination of the pacemaker with a cardioverter/defibrillator is provided by positioning a defibrillator coil near the distal end of the flexible conduit of the pacemaker.

9 Claims, 13 Drawing Sheets

Related U.S. Application Data continuation-in-part of application No. 16/035,653, filed on Jul. 15, 2018, now Pat. No. 10,695,558.

(51) Int. Cl.
*A61N 1/368* (2006.01)
*A61N 1/375* (2006.01)

(58) Field of Classification Search
CPC .......... A61N 5/0622; A61N 7/00; A61N 1/20; A61N 1/32; A61N 1/36017; A61N 7/02; A61N 1/36025; A61N 1/40; A61N 1/36082; A61N 1/362; A61N 2007/0026; A61N 1/3629; A61H 1/005; A61F 7/00; A61F 2007/0002; A61B 8/0816
See application file for complete search history.

(56) References Cited

U.S. PATENT DOCUMENTS

| | | |
|---|---|---|
| 6,600,957 B2 | 7/2003 | Gadsby |
| 6,609,027 B2 | 8/2003 | Kroll |
| 6,684,109 B1 | 1/2004 | Osypka |
| 6,718,206 B2 | 4/2004 | Casavant |
| 6,898,465 B2 | 5/2005 | Gadsby |
| 6,907,299 B2 | 6/2005 | Han |
| 6,937,897 B2 | 8/2005 | Min |
| 7,027,876 B2 | 4/2006 | Casavant |
| 7,082,335 B2 | 6/2006 | Klein |
| 7,089,045 B2 | 8/2006 | Fuimaono |
| 7,228,164 B2 | 6/2007 | Fuimaono |
| 7,245,973 B2 | 7/2007 | Liu |
| 7,302,285 B2 | 11/2007 | Fuimaono |
| 7,326,204 B2 | 2/2008 | Paul |
| 7,326,205 B2 | 2/2008 | Paul |
| 7,326,206 B2 | 2/2008 | Paul |
| 7,440,800 B2 | 10/2008 | Mower |
| 7,729,782 B2 | 6/2010 | Williams |
| 7,819,870 B2 | 10/2010 | Thao |
| 8,021,361 B2 | 9/2011 | Paul |
| 8,078,287 B2 | 12/2011 | Liu |
| 8,162,935 B2 | 4/2012 | Paul |
| 8,332,035 B2 | 12/2012 | Iaizzo |
| 8,391,995 B2 | 3/2013 | Efimov |
| 8,406,899 B2 | 3/2013 | Reddy |
| 8,428,715 B2 | 4/2013 | Ortega |
| 8,437,848 B2 | 5/2013 | Ortega |
| 8,447,399 B2 | 5/2013 | Mower |
| 8,460,286 B2 | 6/2013 | Stangenes |
| 8,538,521 B2 | 9/2013 | Zhu |
| 8,606,369 B2 | 12/2013 | Williams |
| 8,644,927 B2 | 2/2014 | Imran |
| 8,672,936 B2 | 3/2014 | Thao |
| 8,679,109 B2 | 3/2014 | Paul |
| 8,731,662 B2 | 5/2014 | Imran |
| 8,761,880 B2 | 6/2014 | Maskara |
| 8,825,155 B2 | 9/2014 | Zhu |
| 8,838,237 B1 | 9/2014 | Niazi |
| 8,942,805 B2 | 1/2015 | Shuros |
| 8,954,142 B2 | 2/2015 | Ek |
| 8,954,145 B2 | 2/2015 | Lee |
| 9,022,962 B2 | 5/2015 | Brown |
| 9,138,160 B2 | 9/2015 | Imran |
| 9,216,280 B1 | 12/2015 | Hakki |
| 9,289,593 B1 | 3/2016 | Hakki |
| 9,381,361 B2 | 7/2016 | Giovangrandi |
| 9,533,140 B2 | 1/2017 | Ek |
| 9,549,708 B2 | 1/2017 | Mercanzini |
| 9,764,142 B2 | 9/2017 | Imran |
| 2002/0082658 A1 | 6/2002 | Heinrich |
| 2002/0120318 A1 | 9/2002 | Kroll |
| 2003/0040676 A1 | 2/2003 | Prentice |
| 2003/0050637 A1 | 3/2003 | Maguire |
| 2003/0105492 A1 | 6/2003 | Ding |
| 2003/0212436 A1 | 11/2003 | Brown |
| 2004/0064176 A1 | 4/2004 | Min |
| 2005/0131464 A1 | 6/2005 | Heinrich |
| 2005/0267467 A1 | 12/2005 | Paul |
| 2008/0091192 A1 | 4/2008 | Paul |
| 2008/0140139 A1 | 6/2008 | Heinrich |
| 2009/0093859 A1 | 4/2009 | Ortega |
| 2010/0016917 A1 | 1/2010 | Efimov |
| 2010/0228308 A1 | 9/2010 | Cowan |
| 2010/0318147 A1 | 12/2010 | Forslund |
| 2011/0230922 A1 | 9/2011 | Fishel |
| 2012/0101539 A1 | 4/2012 | Zhu |
| 2013/0116740 A1 | 5/2013 | Bornzin |
| 2013/0123870 A1 | 5/2013 | Heinrich |
| 2013/0123872 A1 | 5/2013 | Bornzin |
| 2013/0158621 A1 | 6/2013 | Ding |
| 2014/0067036 A1 | 3/2014 | Shuros |
| 2014/0172035 A1 | 6/2014 | Shuros |
| 2014/0228713 A1 | 8/2014 | Thao |
| 2014/0249604 A1 | 9/2014 | Brown |
| 2014/0276929 A1 | 9/2014 | Foster |
| 2015/0094783 A1 | 4/2015 | Brown |
| 2015/0134022 A1 | 5/2015 | Lee |
| 2015/0151109 A1 | 6/2015 | Ek |
| 2016/0022998 A1 | 1/2016 | Imran |
| 2016/0136434 A1 | 5/2016 | Lee |
| 2016/0346532 A1 | 12/2016 | Shelton et al. |
| 2017/0080210 A1 | 3/2017 | Mercanzini |
| 2017/0087352 A1 | 3/2017 | Ek |
| 2017/0291022 A1 | 10/2017 | Shuros et al. |
| 2018/0214689 A1 | 8/2018 | Zhang |
| 2020/0016395 A1* | 1/2020 | Makharinsky ......... A61N 1/056 |

\* cited by examiner

INTRASEPTAL MULTI-ELECTRODE CARDIAC PACEMAKER AND METHODS OF USE THEREOF

CROSS-REFERENCE DATA

This patent application is a continuation-in-part and claims a priority date benefit of a co-pending U.S. patent application Ser. No. 16/221,547 filed 16 Dec. 2018 and entitled LEADLESS MULTI-ELECTRODE CARDIAC PACEMAKERS AND METHODS OF IMPLANTATION THEREOF, which in turn is a continuation-in-part of a co-pending U.S. patent application Ser. No. 16/035,653 filed 15 Jul. 2018 by the same inventor and entitled SINGLE CONDUIT MULTI-ELECTRODE CARDIAC PACEMAKER AND METHODS OF USING THEREOF, all incorporated herein by reference in their respective entireties.

BACKGROUND

The present invention relates generally to cardiac pacing. More particularly, the invention describes novel devices and methods of physiologic cardiac stimulation using a multi-electrode cardiac pacemaker configured for stimulating ventricular intraseptal area of the heart engaging the natural conduction pathways in the cardiac septum.

His bundle pacing has emerged recently as a useful alternative to traditional single- and multi-chamber pacemaker configurations, especially as a good physiologic alternative to right ventricular pacing. In studies, His bundle pacing has been shown to be associated with a significant reduction in mortality as well as various complications such as heart failure hospitalizations and upgrade to bi-ventricular pacing in comparison to right ventricle pacing in patients with bradycardia and indications for permanent pacemakers (see for example Sharma PS, etc. Permanent His bundle pacing is feasible, safe, and superior to right ventricular pacing in routine clinical practice. *Heart Rhythm.* 2015; 12(2):305-312). Based on a systematic review of the available published literature on physiologic pacing. HBP was incorporated into the recently released 2018 American Heart Association/American College of Cardiology/Heart Rhythm Society guidelines on the evaluation and management of patients with bradycardia and cardiac conduction delay.

At the same time, while His bundle pacing is feasible in the majority of patients requiring ventricular pacing, it may be more challenging to implement in some patients due to existence of high capture thresholds or an inability to correct underlying His-Purkinje conduction disease (see for example Vijayaraman P. His bundle pacing to left bundle branch pacing: evolution of His-Purkinje conduction system pacing. *The Journal of Innovations in Cardiac Rhythm Management,* 2019; 10:3668-3673).

FIGS. 1 and 2 illustrate that this can be explained by the position of the source of conduction abnormalities 22 located distally of the AV node 10 and His bundle 20. FIG. 1 shows the right atrium and intraseptal conduction pathways and FIG. 2 shows how conduction pathways bifurcate distally of the His bundle into right bundle branch 12 and left bundle branch 14, which in turn also splits into Left Posterior Fascicle 16 and Left Anterior Fascicle 18.

To overcome this condition, pacing of left bundle branch 14 and/or right bundle branch 12 at locations distal of the conduction abnormality 22 may be implemented by positioning the pacing electrodes at the intraseptal area of the heart between the right ventricle and left ventricle, see for example positions 12 and 14 in FIG. 1 as examples of such locations.

As discussed in my earlier patent applications, deployment of a pacing electrode aimed to reach intended conduction fibers such as His bundle and provide for pacing with a low capture threshold may be difficult to achieve. Multiple placements of such electrode may be attempted before achieving a satisfactory result. The need therefore exists for devices and methods for improved deployment and operation of cardiac pacemakers configured for stimulation of left and/or right bundle branches of the heart at a location defined by the heart interventricular septum representing a target, which may be easier to reach with a single deployment.

A further uncertainty during deployment of a conventional electrode when used for intraseptal pacing is the location of the conduction fibers for one of both branches of the His bundle. For each branch, it is uncertain as to where the fibers are located so as to minimize the capture threshold. This location uncertainty may be divided into a lateral position uncertainty (radially away from the center of the delivery system) as the electrode is approaching the septal surface and a depth uncertainty as such conduction pathway fibers may be positioned at various depths inside the septum of the heart.

Septum thickness is limited as well as electrode deployment would be done best if it does not protrude/perforate across the septum and emerges on the opposite side of the septal wall. Anatomical variations between subjects may make if difficult to design one or just a few sizes of such electrodes for use with most subjects.

The need exists therefore for a universal design of intraseptal pacemaker configured to be used in most cases without the risk of "under-deployment" or "over-deployment" into the septal tissue.

BRIEF SUMMARY OF THE INVENTION

Accordingly, it is an object of the present invention to overcome these and other drawbacks of the prior art by providing a novel intraseptal multi-electrode cardiac pacemaker configured for electrical stimulation of the heart at an intraseptal location.

It is another object of the present invention to provide either a single-conduit or leadless intraseptal multi-electrode pacemaker configured for implantation at an interventricular septum of the heart in a broad range of patients with a variety of anatomical variations and abnormalities in electrical conduction of the cardiac tissue.

A further object of the present invention is to provide an intraseptal multi-electrode cardiac pacemaker allowing to rapidly identify best stimulation sites after implantation and to provide cardiac pacing without a need to implant multiple individual electrodes.

It is yet another object of the present invention to provide an intraseptal multi-electrode pacemaker configured to stimulate not only one or two ventricles of the heart but also for synchronized stimulation of the right atrium of the heart using the same control unit.

Finally, it is a further object of the present invention to provide a combination of a cardiac pacemaker and an implantable cardioverter/defibrillator, which can be activated as needed or at a later date after activation of the pacemaker for providing heart stimulation therapy to the subject along with lifesaving defibrillation therapy.

In embodiments, the novel intraseptal multi-electrode pacemaker comprises a flexible elongated conduit containing at least a first plurality of individual electrical wires (such as electrical wires 120 and 150 in FIG. 3) operably connected to a plurality of respective first individual electrodes (such as individual electrodes 122 and 152 in FIG. 3) at the distal end of the flexible conduit. In other embodiments, the elongated conduit may also house a second plurality of individual electrical wires operably connected to a respective plurality of second individual electrodes. The plurality of first electrodes extend from the distal end of the conduit by a first distance selected to provide implantation of first electrodes at a depth generally corresponding to a presumed location of conductive fibers of the left bundle branch in the interventricular septum. At the same time, the plurality of second electrodes may be configured to extend from the distal end of the flexible conduit at a second distance selected to implant second electrodes at a depth generally corresponding to a presumed intraseptal location of conduction fibers of the right bundle branch of His bundle. The flexible conduit may further be equipped with a tissue fixation screw, which by itself may house no electrodes, while in other embodiments it may house one or more pacing and/or sensing electrodes.

Following the positioning of the first and/or second pluralities of individual electrodes in and around the target area of the cardiac septum, for example approaching the septum from the right ventricle, individual interrogation of these individual electrodes may be conducted with the aim of identifying selected electrodes located directly at the target site of either the left bundle branch or the right bundle branch, or both. Selected subsets of individual electrodes may be identified as preferred for subsequent cardiac stimulation based on one or more predetermined criterion, for example an intraseptal capture threshold of the LV or RV myocardium via the corresponding bundle branches at or below a predetermined level. Those individual electrodes that do not provide desired cardiac stimulation response during test stimulation may be abandoned and left in a passive state inside the cardiac tissue. If more than one individual electrode is found to satisfy the desired selection criterion, additional selection within this group may be conducted to identify one or more individual electrodes with the lowest capture threshold for effective cardiac stimulation.

The step of re-evaluating some or all of the individual electrodes may be repeated from time to time, for example when a failure of one or more of the individual electrodes is detected. Upon completion of such re-evaluation, the same or a different subset of individual electrodes may be selected to provide pacing therapy to the heart of the subject.

In further embodiments, additional atrial electrodes may be provided for stimulating a right atrium of the heart so that the entire cardiac pacing therapy may be delivered from a single control unit. Such one or more additional individual electrodes may be configured for implantation into a variety of subjects with a broad range of anatomical variations and still provide at least one atrial electrode with an acceptable cardiac pacing performance.

Finally, a combination of a multi-electrode cardiac pacemaker and an implantable cardioverter/defibrillator is described in which one or more defibrillator coils may be positioned at the distal end of the flexible conduit and used as a mechanical stop to limit the depth of implantation of the multiple individual electrodes of the cardiac pacemaker. In further embodiments, one or more of the coils of the defibrillator portion of the device may be used as intermittently- or continuously-operated sensing electrodes during the initial evaluation and/or subsequent use of the pacemaker electrodes.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
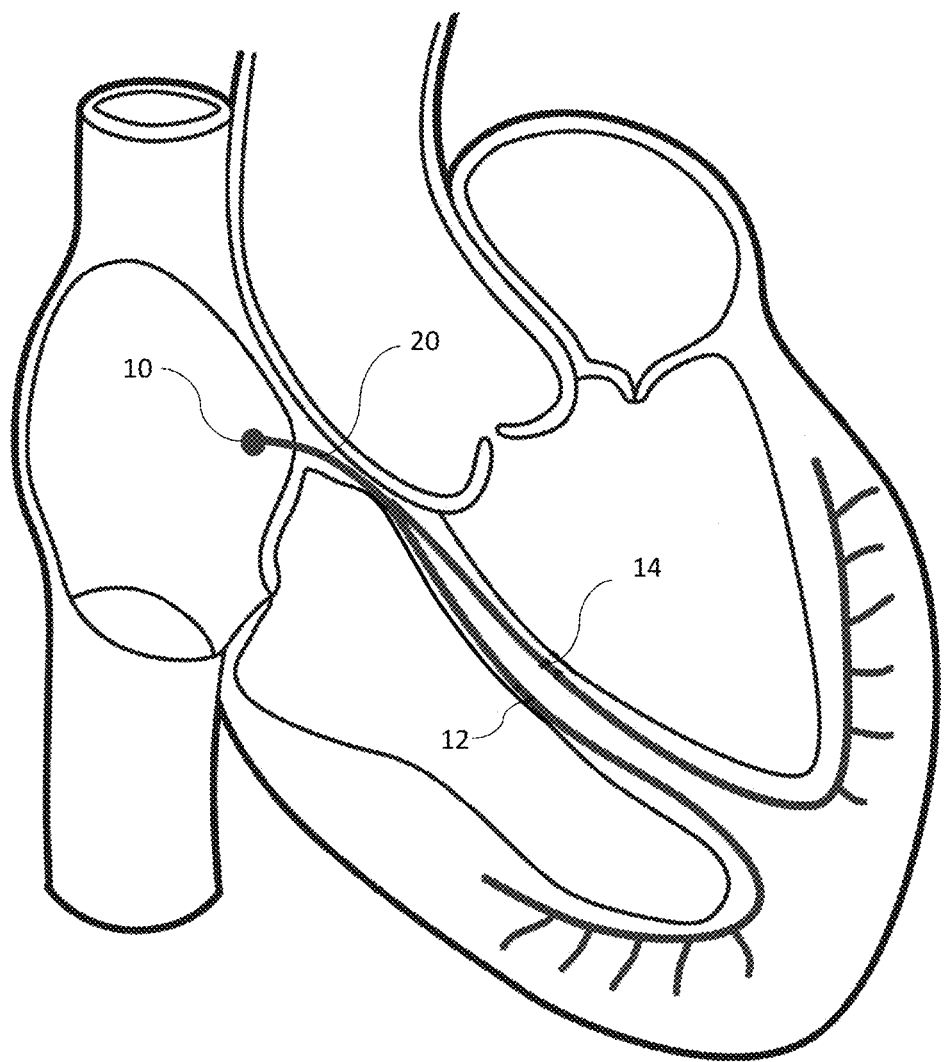
FIG. 1 is a general cross-sectional view of a heart showing a general anatomical location of the conduction pathways within the right atrium and interventricular septum.
Figure 2:
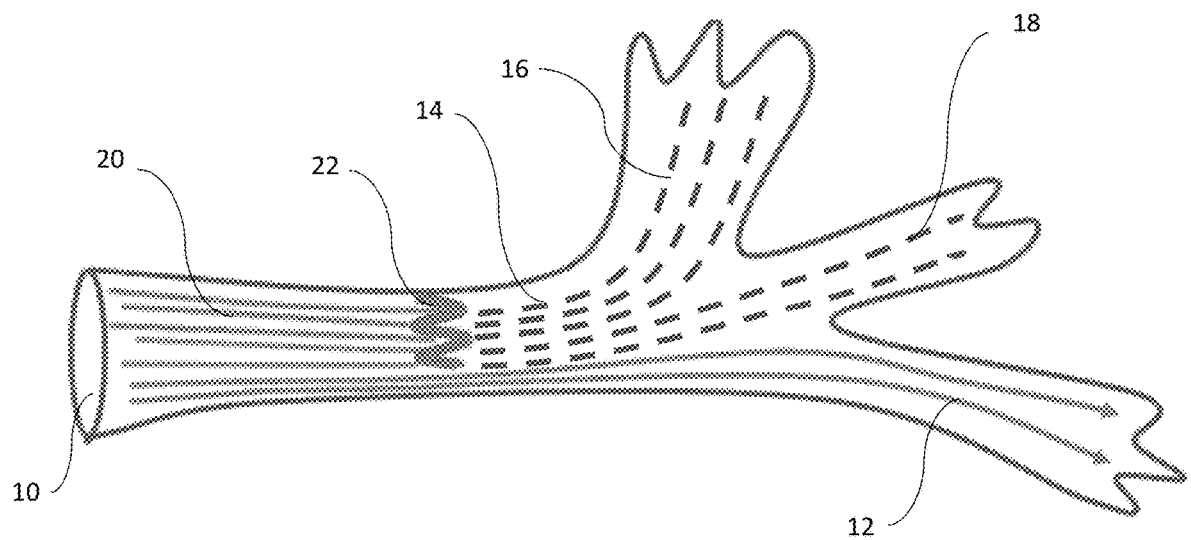
FIG. 2 is a schematic view of a conduction fibers extending from the His bundle and bifurcating into a left bundle branch and a right bundle branch.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The term "multi-electrode pacemaker" is used herein to describe both a single-conduit multi-conductor design connecting a plurality of individually-operable electrodes inside a heart of the subject and attached to a cardiac pacemaker unit located elsewhere inside or outside the body of the subject; as well as a leadless cardiac pacemaker operably connected to this plurality of individual electrodes.

Figure 3:
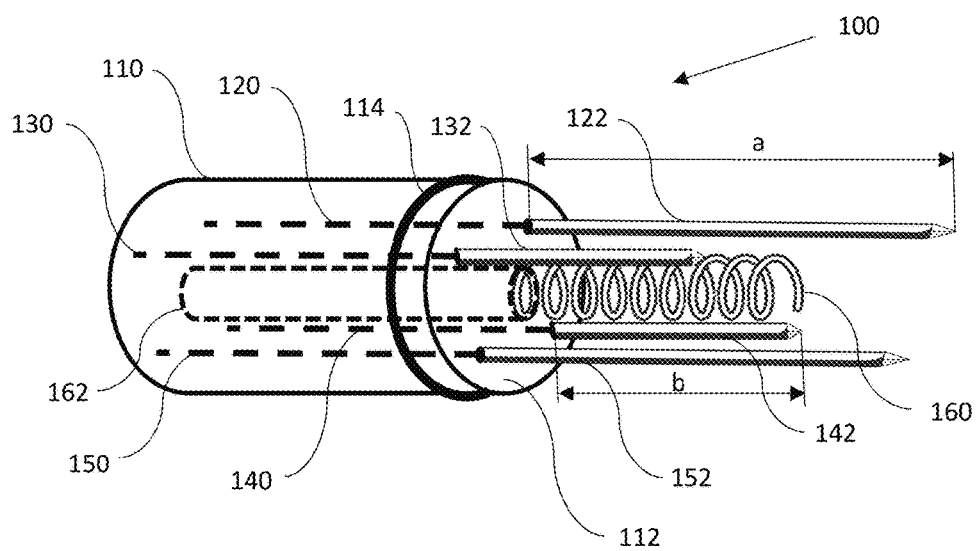
FIG. 3 is a perspective view of a distal end of the intraseptal multi-electrode cardiac pacemaker according to the first embodiment of the invention.

FIG. 3 shows a first embodiment of the intraseptal multi-electrode cardiac pacemaker 100 of the present invention. Shown in FIG. 3 is a distal end 112 of the flexible conduit 110. The proximal end of the flexible conduit 110 is designed to be connected to a pacemaker controller (not shown) located in a subcutaneous clavicle pocket or another subcutaneous location elsewhere in the body as the invention is not limited in this regard. Flexible conduit 110 may be designed to traverse a portion of a blood vessel such as superior or inferior vena cava in order to connect the pacemaker controller located outside the heart to a location inside the heart where individual electrodes may be implanted, such as an interventricular septum.

The flexible conduit 110 may be configured to house a plurality of first individual electrical wires positioned in parallel to each other and extending inside the conduit—such as electrical wires 120 and 150 seen in FIG. 3. In some embodiments, some or all of the plurality of individual wires may be fixedly imbedded in the flexible conduit 110, while in other embodiments, the conduit 110 may have respective slots configured for at least some or all of the plurality of individual electrical wires to be slidably retained therein. In further embodiments, some of the individual electrical wires may be fixedly attached inside the flexible conduit 110 while other individual electrical wires may be retained inside with the ability to slide along the conduit 110. Fixedly attached individual electrical wires may be used with designs that do not involve moving individual electrodes to extend them from the distal end 112 of the conduit 110, while slidable retention of individual electrical wires may be used when such movement of individual electrodes is desired—as will be explained in greater detail below.

A plurality of first individual electrodes may be positioned to extend from the distal end 112 of the flexible conduit 110. In embodiments, there may be 2, 3, 4, 5, 6, 7, 8, 9, 10, 11, 12, 13, 14, 15, 16 or more first individual electrodes present. FIG. 3 shows a design with two first electrodes 122 and 152. The plurality of first electrodes may be designed to protrude from the distal end 112 of the flexible conduit 110 by a predetermined first distance a selected to cause the ends of the first individual electrodes to be positioned in the interventricular septum so as to operably reach the conduction fibers of the left bundle branch.

A typical non-hypertrophic interventricular septum is about 8 to 11 mm in width, such as at a location about 2-3 cm below the tricuspid valve, a common place for implantation of intraseptal pacing electrodes. Hypertrophy is frequently present making it thicker than 11 mm—in some cases as much as 20 mm. Most of the conduction fibers of the right bundle branch may be located closely to the side of the septum facing the right ventricle, for example about 0.5 mm, 1 mm, 2 mm, 3 mm, 4 mm, 5 mm, or up to about 6 mm below the septum surface facing the right ventricle. At the same time, a similar depth distribution of conduction fibers of the left bundle branch of about 6 mm or less from the surface may be observed close to the other surface of the septum, this one facing the left ventricle. When the depth of position of the left bundle branch conduction fibers inside the intraventricular tissue is measured from the right ventricular side, depending on the overall thickness of the septum, that measurement may be more than about 4 mm, such as 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or about 20 mm depending on the presence and the degree of the septal hypertrophy or thickening.

Therefore assuming the distal end 112 abuts against the right ventricular side of the intraventricular septum, the first distance a for the length of protrusion of the plurality of first electrodes may be selected to be about 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or about 20 mm. This will assure that the plurality of first individual electrodes will reach the area of the intraventricular septum in close proximity to the conduction fibers of the left bundle branch so as to be in operable reach thereof and provide intraseptal capture at low voltage thresholds. The term "intraseptal capture" is broadly used herein to describe capture of the conduction system fibers located within the interventricular septum and may include capture of a left bundle branch, right bundle branch or both.

In embodiments, only a distal tip of one or more of the plurality of first individual electrodes may be exposed to be electrically active when in contact with cardiac tissue, with the rest of the length of the individual electrode body being insulated. In this case, most of the electrical current will penetrate the cardiac tissue from the electrode tip, rather then being distributed from the entire length of the individual electrode. Yet in other embodiments, the entire length of first individual electrodes may be made from a conductive material such as metal for simplicity of design.

In addition to the plurality of first individual electrodes, the flexible conduit 110 may contain a plurality of second individual electrical wires extending therethrough and terminating at the distal end 112 thereof with corresponding plurality of second individual electrodes. The number and design of second individual electrical wires and second individual electrodes may be similar to that of first individual electrical wires and first individual electrodes—with one important difference, namely the second distance b of protrusion of second individual electrodes from the distal end 112. The second distance b may be selected to cause the plurality of second individual electrodes to be deployed in the interventricular septum in such a way as to be in close vicinity and operably in reach of the conduction fibers of the right bundle branch of the septum.

FIG. 3 illustrates an exemplary design of the flexible conduit 110 with two of the second individual electrical wires 130 and 140 terminating with respective second individual electrodes 132 and 142, which are shorter that first individual electrodes so as to deploy to be in vicinity of right bundle branch. The second distance b in this case may be selected to be about 0 mm, 0.5 mm, 1 mm, 2 mm, 3 mm, 4 mm, 5 mm, 6 mm or any distance in between so that the plurality of second individual electrodes are deployed closer to the surface of the septum facing the right ventricle. The distance of 0 mm may be achieved by simply positioning a plurality of second individual electrodes made as individual conductive dots on the distal end 112 of the non-conductive flexible conduit 110.

A tissue attachment screw 160 may also be provided at the distal end 112 of the flexible conduit 110. The depth of penetration into the cardiac tissue of the tissue attachment screw 160 may be selected to not exceed the septum thickness so as to not protrude on the opposite side when deployed from the right ventricular side of the heart. The diameter and pitch of the tissue fixation screw may be selected following normal design practices for single electrode intraseptal pacing devices. In this embodiment, the tissue attachment screw 160 may be positioned close to a center of the distal end 112 with the pluralities of first and second individual electrodes positioned outside the tissue attachment screw 160 along the periphery of the distal end 112.

Two alternative designs for a combination of a tissue attachment screw and a plurality of individual electrodes are contemplated by the present invention: (1) with a fixedly attached tissue attachment screw to the body of the flexible conduit and sliding individual electrodes inside thereof, and (2) with fixed individual electrodes and independently rotatable tissue attachment screw.

The first design involves a step of retracting all individual electrodes inside the body of the flexible conduit 110 to position them proximally of the tissue attachment screw 160 prior to deployment. Once the distal end of the fixedly attached tissue attachment screw 160 abuts against the septum, the flexible conduit 110 as a whole may be rotated to cause the tissue attachment screw 160 to engage with the cardiac tissue and after a predetermined number of revolutions secure the distal end 112 of the flexible conduit 110 against the septal tissue surface. After that, a plurality of first and/or second individual electrodes may be moved forward (individually or as a group) to emerge from the distal end 112 and extend into the septal tissue by a respective first distance or a second distance.

The second design involves an optional rotatable component such as a flexible rod or wire 162 connected to the tissue attachment screw 160. The flexible rod may be operated from the proximal end of the flexible conduit 110. Upon positioning the distal end 112 next to the septal wall, the flexible rod 162 may be used to engage the tissue attachment screw 160 with cardiac tissue and cause implantation of the plurality of first and/or second individual electrodes fixedly extended from the distal end 112 into the interventricular septum—by rotating the flexible rod 162 and deploying the tissue attachment screw 160 into the cardiac tissue. In this case, the flexible conduit 110 is not rotated as a whole but only serves as an outer housing for the rotating flexible rod 162.

The tissue attachment screw 160 may also be used as one of the individual first or second electrodes, while in other embodiments, it may be made as electrically non-active component of the device.

In embodiments, one or more electrode rings 114 may be positioned at the distal end 112 of the flexible conduit 110 and configured to serve as sensing electrodes or as anode electrodes for pacing purposes.

Figure 4:
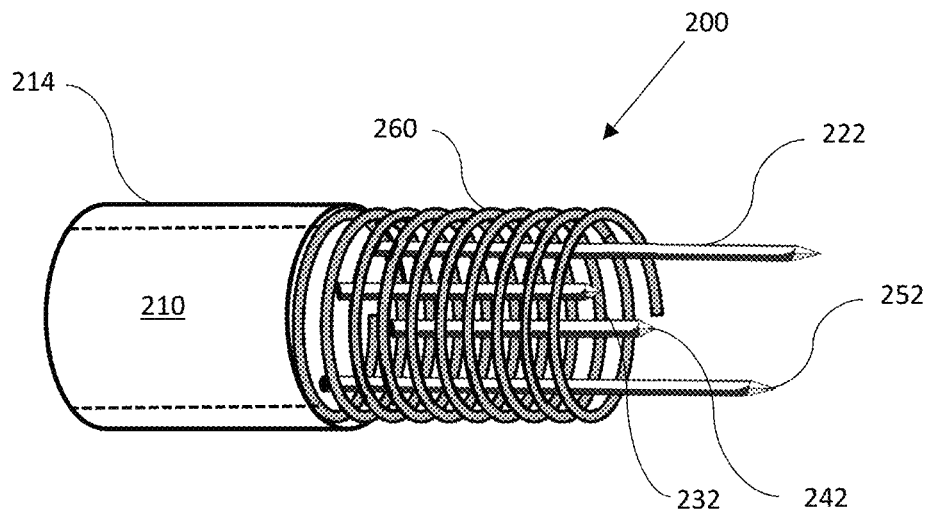
FIG. 4 is a perspective view of a distal end of the intraseptal multi-electrode cardiac pacemaker according to the second embodiment of the invention.

FIG. 4 shows a flexible conduit 210 of a second broad embodiment 200 of the present invention, in which the tissue attachment screw 260 may have a diameter close to that of the outside diameter of the flexible conduit 210 and all of the first individual electrodes 222 and 252 as well as all second individual electrodes 232 and 242 are positioned inside the tissue attachment screw 260. As described above, this design may also be made in two alternative configurations: (1) one design with the tissue attachment screw 260 fixedly attached to the distal end of the flexible conduit 210 and slidable retractable first and second individual electrodes, and (2) a separately rotatable tissue attachment screw 260 (such as activated by an optional rotatable sleeve 214 placed over flexible conduit 210 and first/second individual electrodes 222, 232, 242, 252 fixedly attached to the flexible conduit 210 and extending therefrom by a respective first or second distance as described above.

Figure 5:
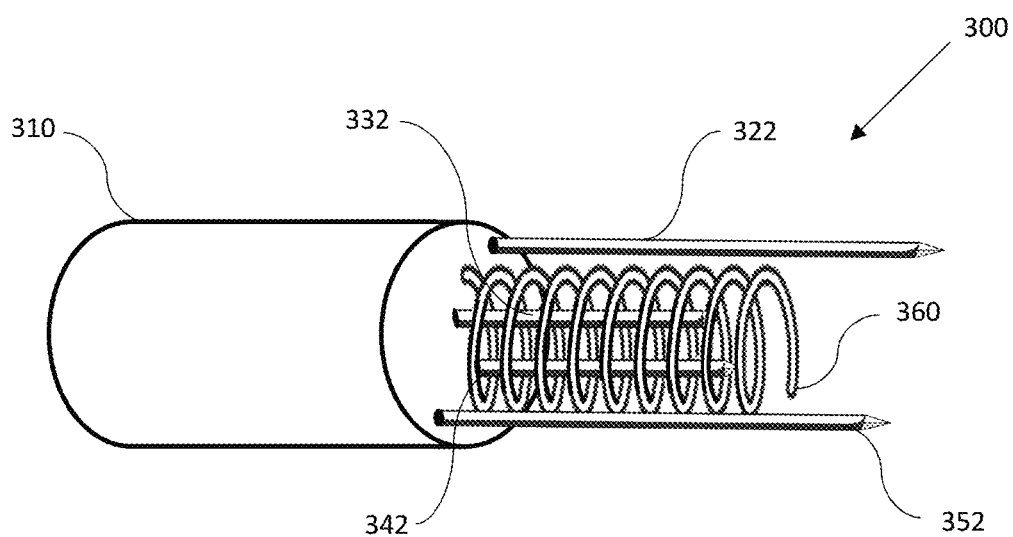
FIG. 5 is a perspective view of a distal end of the intraseptal multi-electrode cardiac pacemaker according to the third embodiment of the invention.

FIG. 5 shows a third embodiment 300 of the present invention in which the tissue attachment screw 360 is made with a medium diameter selected to allow a plurality of first individual electrodes 322 and 352 to be positioned outside thereof close to a periphery of the flexible conduit 310, while the plurality of second individual electrodes 332 and 342 are positioned inside the tissue attachment screw 360.

Figure 6:
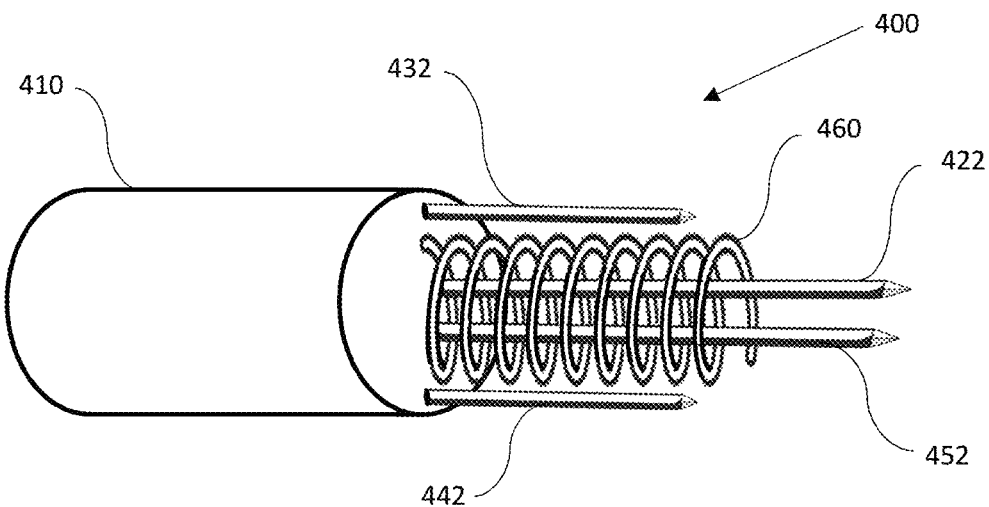
FIG. 6 is a perspective view of a distal end of the intraseptal multi-electrode cardiac pacemaker according to the fourth embodiment of the invention.

FIG. 6 shows a fourth embodiment 400 of the present invention in which the tissue attachment screw is located at the distal end of the flexible conduit 410 and surrounds a plurality of first individual electrodes 422 and 452 positioned close to a center line extending through the flexible conduit 410. A plurality of second individual electrodes 432 and 442 may be positioned in this case outside the tissue attachment screw 460 closer to the periphery of the flexible conduit 410.

Figure 7:
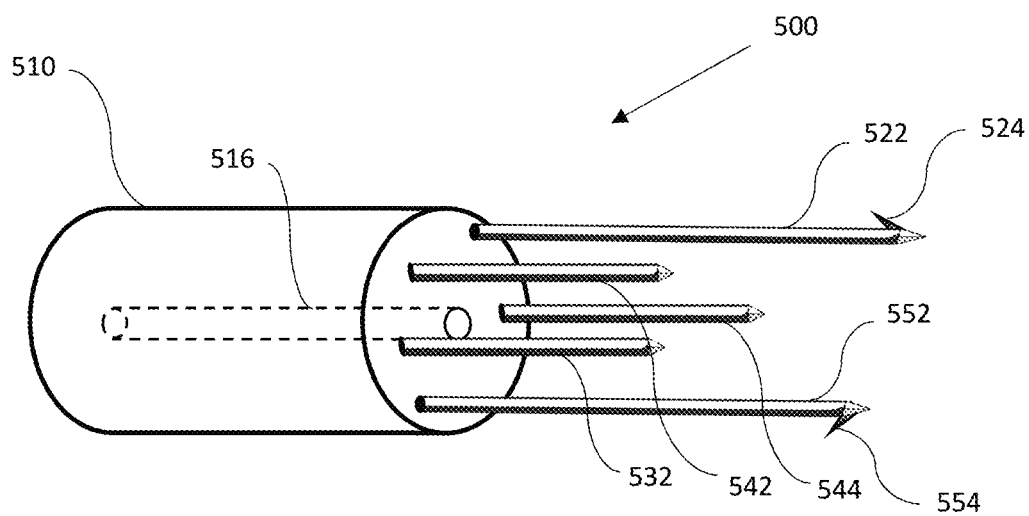
FIG. 7 is a perspective view of a distal end of the intraseptal multi-electrode cardiac pacemaker according to the fifth embodiment of the invention.

A further embodiment of the present invention is illustrated in FIG. 7, showing a design of the fifth embodiment 500 lacking a tissue attachment screw. Instead, at least one or more first or second individual electrodes may be equipped with tissue engagement hooks or other similar elements. In an example shown in FIG. 7, a plurality of first individual electrodes 522 and 552 each feature a respective hook 524 and 554. Also shown in FIG. 7 are three second individual electrodes 532, 542 and 544 extending from the distal end of the flexible conduit 510 by a second and shorter distance than that of the first individual electrodes 522 and 552. One advantage of this design is that it can be made as a single body without any movable parts inside thereof (as compared with previously described embodiments), which may simplify implantation and insertion procedure and increase reliability and longevity of the product.

A further notable element of the design shown in this embodiment is a central lumen 516, which may extend from the proximal end of the flexible conduit to its distal end. The central lumen 516 may be used during deployment of the flexible conduit 516 in one of several ways: (a) to allow sliding the flexible conduit 510 over a guidewire already positioned in the heart of the subject, (b) to monitor blood pressure and optionally determine the location of the distal end of the flexible conduit based on a pressure waveform reading, or (c) to insert a removable stylet inside the flexible conduit 510. Such removable stylet may be used to temporarily increase the stiffness of the flexible conduit during implantation procedure and/or apply a predetermined curve to the shape of the flexible conduit by using a malleable or pre-formed stylet having a desired shape suitable for a particular subject. Following insertion and implantation of the flexible electrode into the heart, the proximal end of the central lumen may be capped off.

Figure 8:
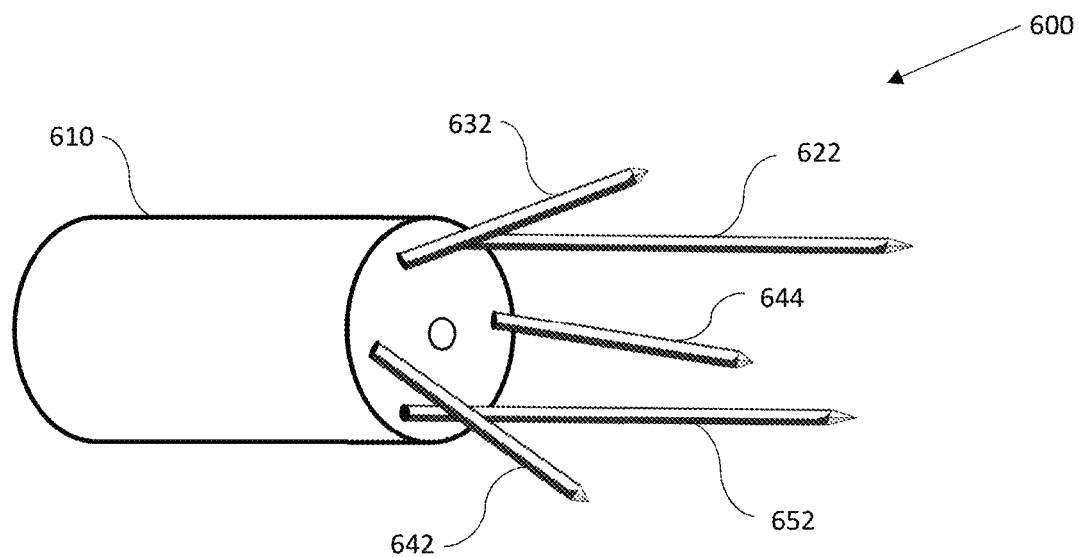
FIG. 8 is a perspective view of a distal end of the intraseptal multi-electrode cardiac pacemaker according to the sixth embodiment of the invention.

Flexible conduit 600 according to the sixth embodiment of the present invention is shown in FIG. 8. One or several of the retractable individual electrodes may be pre-formed and configured to extend radially away from the center of the conduit upon implantation. In one example, the plurality of first individual electrodes 622 and 652 may be designed to be similar to that described above and may be fixedly attached to and extend from the distal end of the flexible conduit 610. At the same time, three of the second individual electrodes 632, 642, 644 may be preformed so as to expand radially away from the center of the flexible conduit when they are caused to emerge from the body of the flexible conduit upon implantation. The steps of deployment of the flexible conduit 610 in this case may include retraction of second individual electrodes 632, 642, 644 inside the body of the conduit 610; positioning of the distal end of the conduit 610 adjacent the a target implantation site (optionally with a guidewire or stylet advanced via a central lumen), advancement of the plurality of first individual electrodes 622, 652 into the cardiac tissue; and pushing the second individual electrodes 632, 642, 644 forward (individually or as a group) to emerge from the distal end of the conduit 610 and expand in different directions away from the center of the flexible conduit 610. Placement of individual electrodes this way may be sufficient to secure the flexible conduit 610 to the interventricular septum without a need for any additional fixation means such as a tissue attachment screw as shown in other embodiments of the invention.

Figure 9:
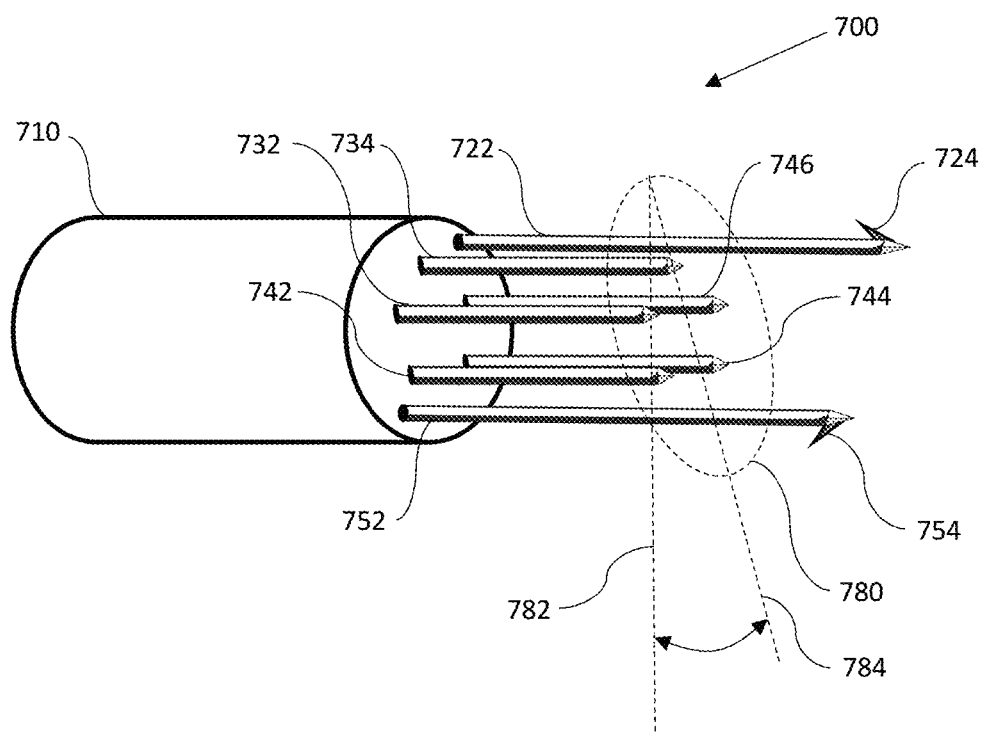
FIG. 9 is a perspective view of a distal end of the intraseptal multi-electrode cardiac pacemaker according to the seventh embodiment of the invention.

FIG. 9 shows a seventh embodiment 700 of the present invention. In this embodiment, the distal end of the flexible conduit 710 features a plurality of first individual electrodes 722 and 752, optionally equipped with tissue retention hooks 724 and 754. It also contains a plurality of second individual electrodes—five in this example shown as electrodes 732, 734, 742, 744, 746. The tips of second electrodes may be arranged to define a plane 780, which may be slightly tilted by an angle between the lines 784 from the plane 780 and the line 782 parallel to the end of the flexible conduit 710. The purpose of the tilting of the plane 780 is to effectively position second electrode tips at a slightly different distance from the end of the flexible conduit 710. When these second electrodes are implanted into the tissue, the tilting of the plane 780 defined by their respective electrode tips would increase the probability of operatively reaching the conduction fibers of the right bundle branch, which may be located at slightly different depths between different subjects. In embodiments, the angle of tilting of the plane 780 may be from about 10 degrees to about 50 degrees, such as about 10 degrees, about 15 degrees, about 20 degrees, about 25 degrees, about 30 degrees, about 35 degrees, about 40 degrees, about 45 degrees, about 50 degrees, or any angle inbetween as the invention is not limited in this regard.

In further embodiments, the individual electrode tips of the plurality of second individual electrodes may be positioned at a range of second distances from the distal end of the flexible conduit 710 using another similar arrangement, for example having the spread between the shortest second individual electrode and the longest second individual electrode of about 2 mm to about 5 mm.

Similarly, the same small variation of the lengths of the plurality of first individual electrodes is contemplated to be within the scope of the present invention. In one example, the plurality of first individual electrodes may be designed to have a range of first distances defining the lengths of respective first individual electrodes between about 10 mm and about 15 mm when fully extended from the distal end of the conduit 710 and inserted into the interventricular septum wall of the heart.

Figure 10:
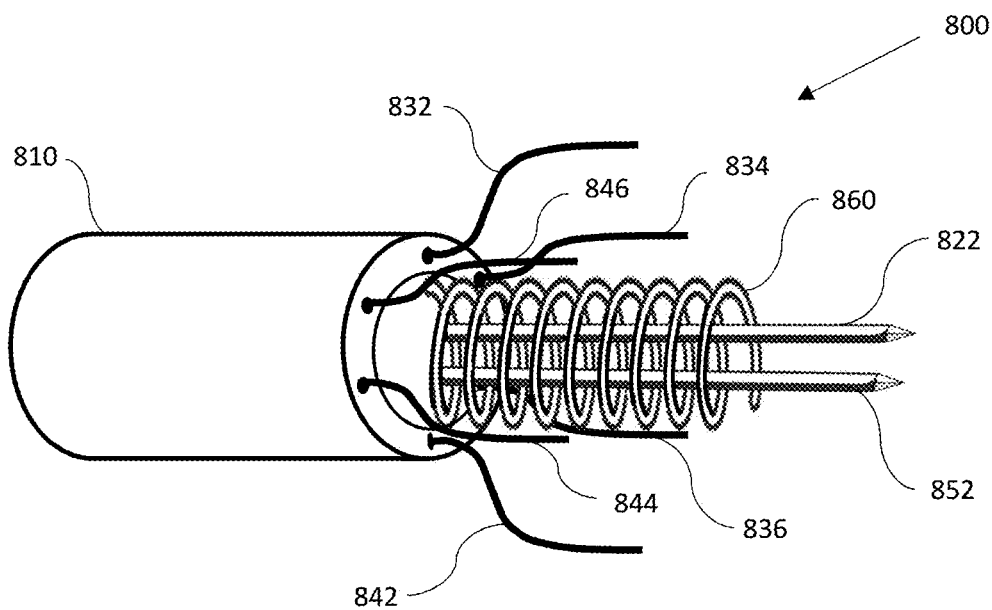
FIG. 10 illustrates a perspective view of a distal end of the intraseptal multi-electrode cardiac pacemaker according to the eighth embodiment of the invention.

Shown in FIG. 10 is the eight embodiment of the flexible conduit 800 of the invention in which at least some of the individual electrodes are made to expand radially or laterally away from the center of the conduit 810. In one example, a plurality of six second individual electrodes 832, 834, 836, 842, 844, and 846 are made from using preformed wires that may be configured to spring outwards when the distal end of the flexible conduit 810 emerges from the delivery catheter. The tissue attachment screw 860 may be made to rotate around the longitudinal axis of the conduit 810. Alternatively, all individual electrodes including first individual electrode 822 and 852 may be made to be retractable to facilitate rotation of the flexible conduit for the purpose of securing it to the interventricular septum. Expanding the individual electrodes beyond the diameter of the flexible conduit 810 may be advantageous in covering a larger area of the interventricular septum in order to maximize the probability of deploying at least one or some of the individual electrodes in closer proximity to the conduction fibers network inside the septum.

In further embodiments, the flexible individual electrodes configured to expanding from the center of the flexible conduit may be made to be of a suitable length to serve as first electrodes, second electrodes or both as the invention is not limited in this regard.

Figure 11:
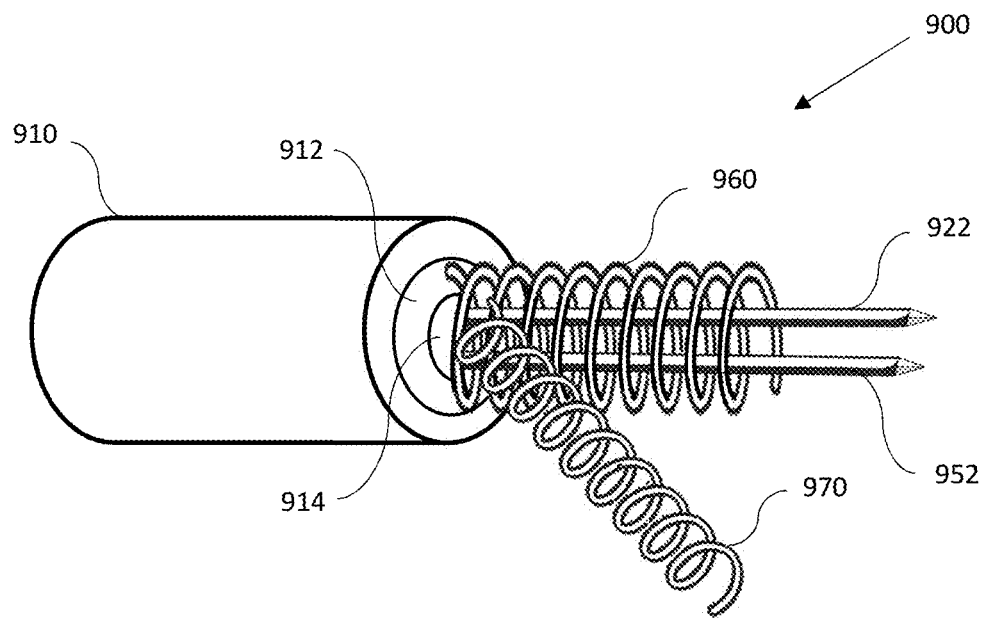
FIG. 11 illustrates a perspective view of a distal end of the intraseptal multi-electrode cardiac pacemaker according to the ninth embodiment of the invention.

FIG. 11 shows a ninth embodiment of the present invention. The flexible conduit 900 of this design may feature a distal end 910 equipped with not one but two initially concentric tissue attachment components: a first tissue attachment screw 960 may be aligned along the longitudinal axis of the conduit 900 and may be independently rotatable inside thereof using the flexible rod 912. At the same time, a second tissue attachment spring 970 may be shaped for deployment diagonally away from the center of the conduit 900. Initially, the second tissue attachment spring 970 may be retracted inside the tissue attachment screw 960 by independently rotating thereof using a flexible rod 914 to move it backwards and inside the inner cavity of the conduit 900. Upon initial deployment of the first individual electrodes 922 and 952 as well as the first tissue attachment screw 960, the second tissue attachment spring 970 may be turned in a suitable direction to cause it to emerge between the turns of the first tissue attachment screw 960. Further rotation of the second tissue attachment spring 970 by turning the flexible rod 914 will cause it to advance sideways and diagonally away from the center of the flexible conduit 910. The second tissue attachment spring 970 may carry one or more individual electrodes thereon so as to serve as a means for sensing or stimulating the right bundle branch of the heart.

Figure 12:
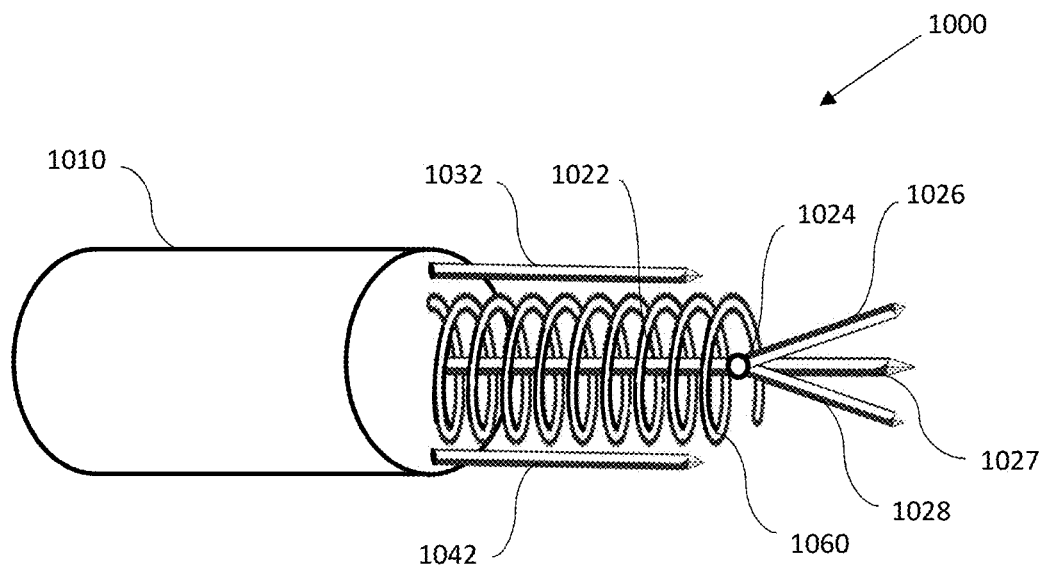
FIG. 12 illustrates a perspective view of a distal end of the intraseptal multi-electrode cardiac pacemaker according to the tenth embodiment of the invention.

A tenth embodiment of the flexible conduit 1000 is shown in FIG. 12. A set of first individual electrodes may be made by bifurcating or trifurcating at least one or more of the first individual electrodes at the distal tip thereof to (i) improve tissue retention of the device inside the cardiac septum and (ii) to provide additional points of contact for the individual electrodes of the pacemaker of the invention. In one example shown in FIG. 12, the distal end 1010 of the flexible conduit 1000 may be equipped with a tissue attachment screw 1060 and a plurality of second individual electrodes 1032, 1042 in a manner similar to the previously described embodiments. The plurality of first individual electrodes may include a common stem 1022 branching out at a common point 1024 into three individual electrodes 1026, 1027, and 1028.

In further embodiments, the side branches 1026 and 1028 may be retained next to the central electrode 1027 as long as the entire first individual electrode 1022, 1026, 1027, 1028 is positioned inside the tissue attachment screw 1060, which may be made to have an internal diameter suitable for keeping all electrodes 1026, 1027, 1028 together. Upon deployment of the tissue attachment screw 1060 and advancing of the stem 1022 forward and away from the distal end of the flexible conduit 1010, the individual electrodes 1026 and 1028 may spring away from the center electrode 1027 to form a trifurcation shown in FIG. 12, which will further improve tissue fixation of the flexible conduit 1000 at the implantation site of the interventricular septum of the heart.

Figure 13:
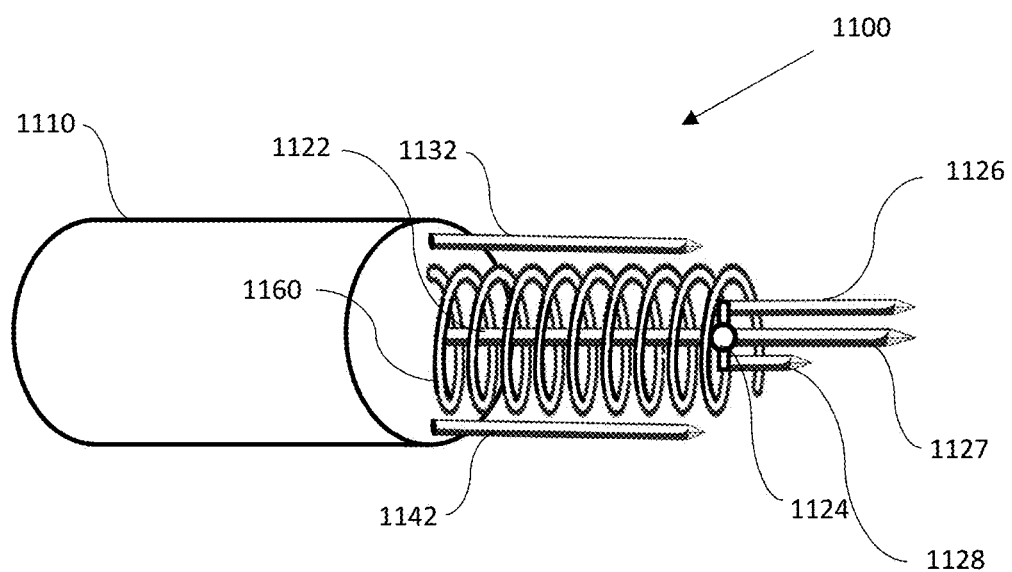
FIG. 13 illustrates a perspective view of a distal end of the intraseptal multi-electrode cardiac pacemaker according to the eleventh embodiment of the invention.

Another yet eleventh embodiment 1100 is shown in FIG. 13. The flexible conduit 1110 may feature a distal end equipped with a plurality of second electrodes 1132, 1142 and a tissue attachment screw 1160 made in manner similar to the previous, tenth embodiment of the invention. The trifurcation point 1124 on a stem 1122 is different in a way to provide at least one of the individual electrodes 1124 to extend from the distal end of the flexible conduit 1110 by a shorter distance than other first electrodes 1126 and 1127. Providing individual electrodes 1126, 1127, 1128 or more protruding at different distances from the distal end of the flexible conduit 1110 may be advantageous in two ways:
  (i) in case that distance difference between electrode tips is less than about 5 mm, the plurality of first individual electrodes may have a better probability of reaching the conduction fibers of the left branch, which may be located at anatomically different distances from the distal end of the flexible conduit 1110, as explained above in greater detail, and
  In case the difference in distance between electrode tips is between about 6 mm and about 10 mm, some of the individual electrodes may be assumed to be deployed to operably reach the left bundle branch conduction fibers, while others may be expected to operably reach the right bundle branch conduction fibers. In this case, the design may be simplified by obviating a need to provide individual electrodes 1132, 1142 outside of the tissue attachment screw 1160.

Figure 14:
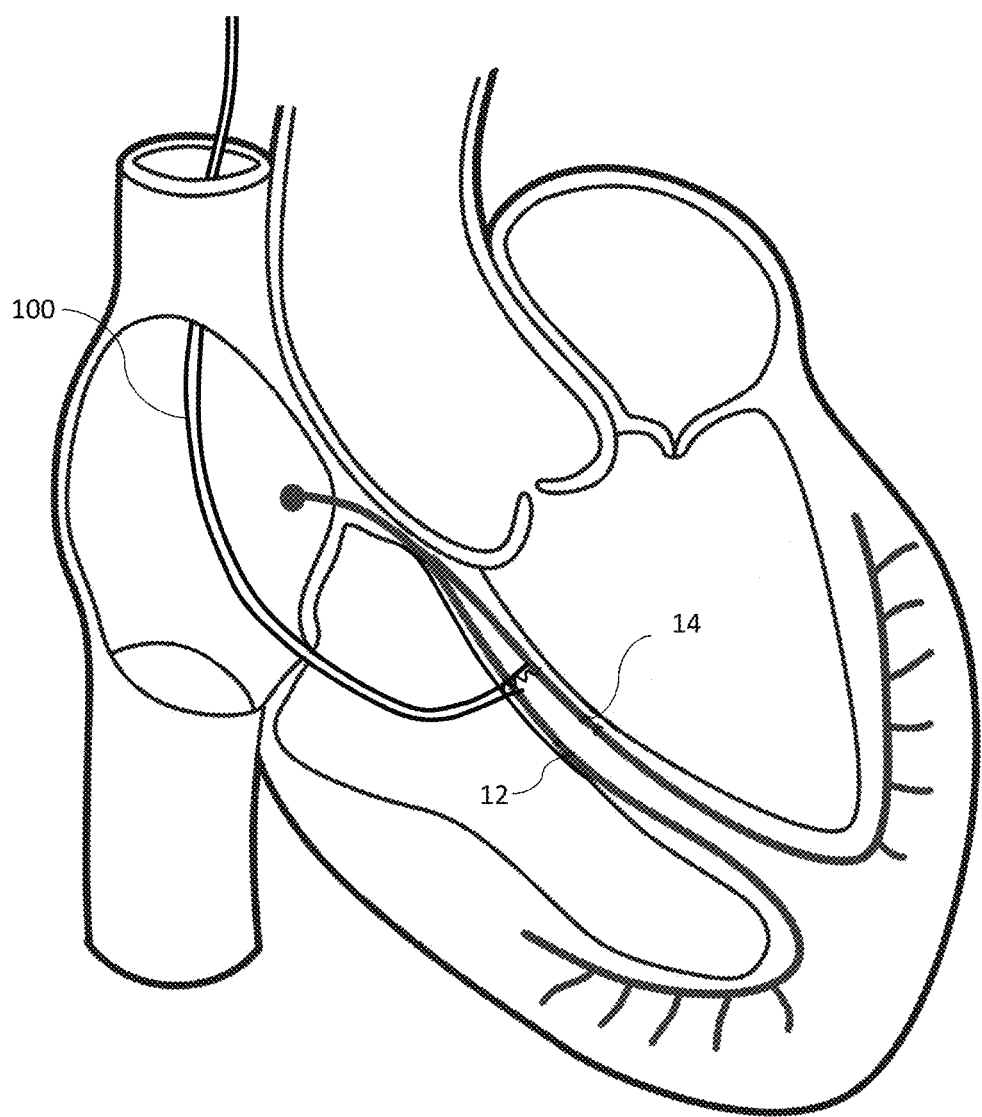
FIG. 14 shows one suitable implantation approach for any of the described embodiments of the intraseptal multi-electrode cardiac pacemaker of the present invention.

FIG. 14 shows an exemplary implantation of the flexible conduit 100 in the heart of the subject. A typical approach may be from superior vena cava and into the right atrium of the heart. The flexible conduit may be then extended into the right ventricle and positioned such that the distal end thereof may be facing the interventricular septum wall from the side of the right heart of the subject—as seen in the drawing. Tissue attachment screw may be then activated or in other embodiments at least a plurality of first individual electrodes may be deployed into the septum wall. Once all desired individual electrodes are deployed and the distal end of the flexible conduit 100 is secured to the septum wall, the process of interrogation of the individual electrodes may be started as described below in greater detail.

As mentioned above, the term "flexible conduit" is used interchangeably for the purposes of this description with the term "leadless pacemaker" in a way that all embodiments described herein with the reference to a flexible conduit may be easily adopted to application with a leadless pacemaker as can be understood by a person skilled in the art. To illustrate one such embodiment, FIG. 15 shows a leadless pacemaker 1200 implanted in the interventricular septum in a manner similar to that shown in the previous figure.

Figure 15:
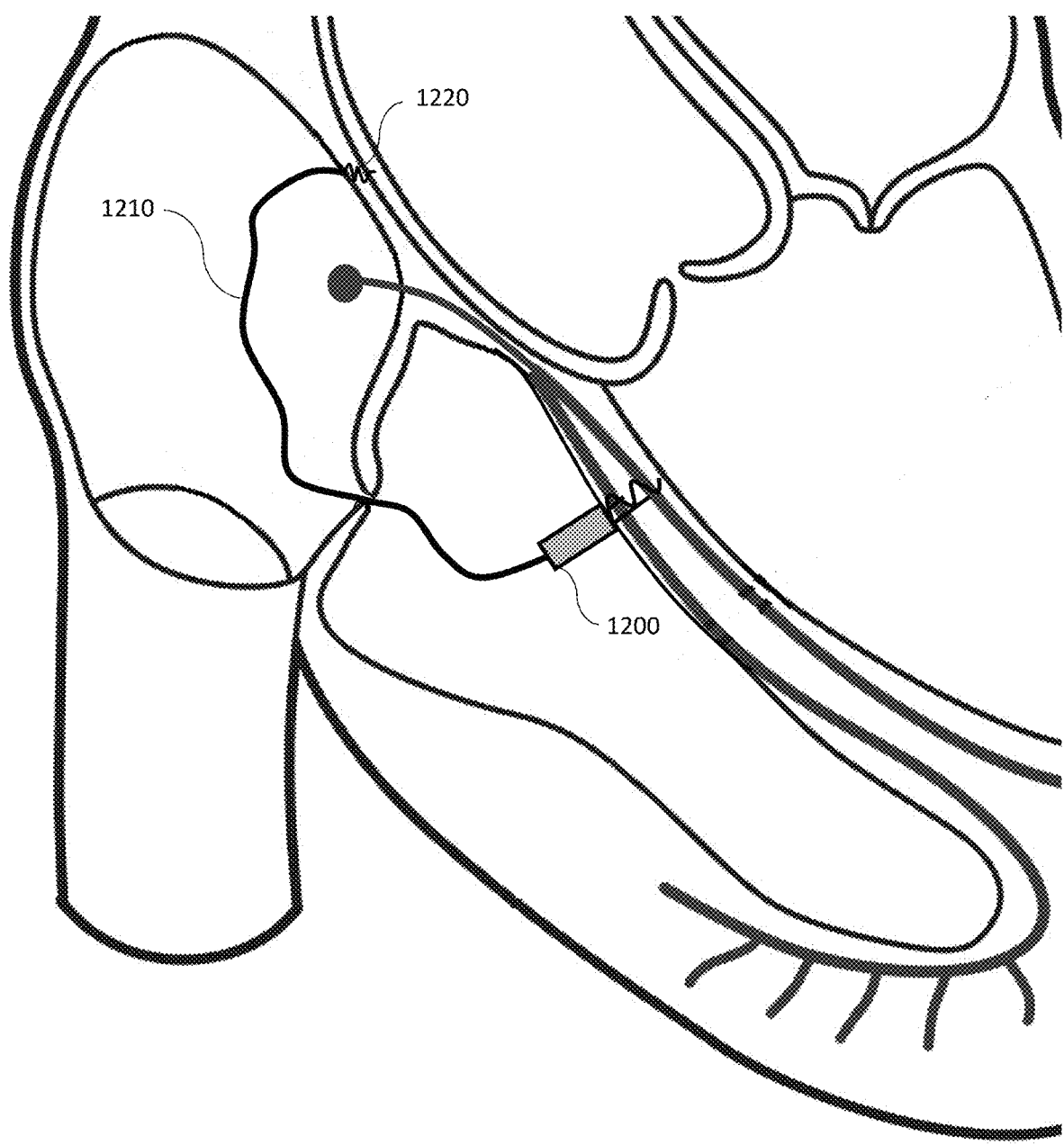
FIG. 15 shows yet another embodiment of the present invention in which a leadless multi-electrode pacemaker is equipped with a supplemental atrial stimulation electrode.

In addition, FIG. 15 shows at least one atrial electrode 1220, which may be attached to the leadless pacemaker 1200 by an individual wire 1210. In this case, the leadless pacemaker may be configured for stimulation of the right atrium in addition to pacing the left and/or the right ventricle of the heart. The additional atrial electrode 1220 may be deployed after the implantation of the leadless pacemaker 1200, such as during retraction of the delivery system configured for deployment of the leadless pacemaker 1200.

Figure 16:
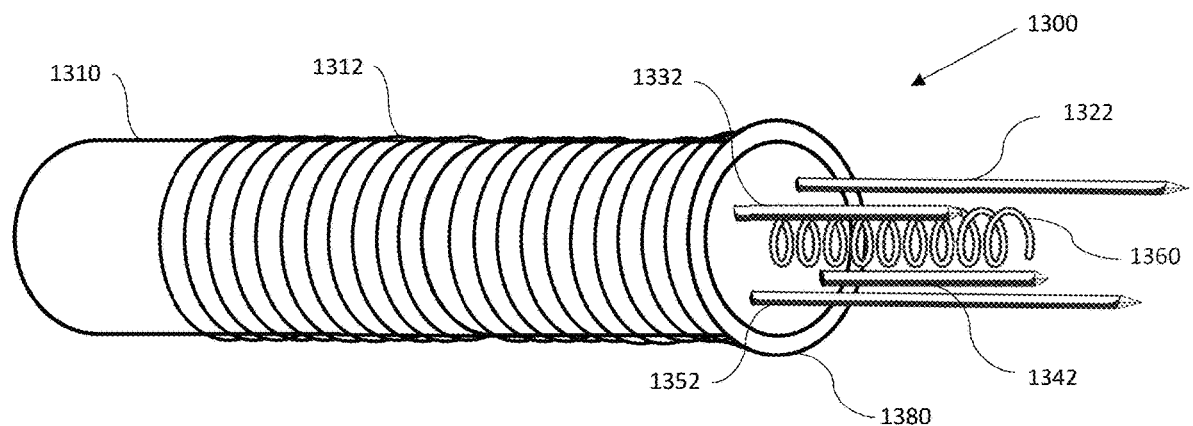
FIG. 16 shows a distal end of a combination of intraseptal multi-electrode pacemaker of the present invention with an implantable coil of a cardioverter/defibrillator.

In further embodiments of the present invention shown in FIG. 16, a defibrillator coil 1312 (or several defibrillator coils in series) may be positioned at the distal end 1310 of the flexible conduit 1300. Shown here is a design of a flexible conduit 1300 similar to that of the first embodiment of the present invention and equipped with a plurality of first individual electrodes 1322, 1352 and a plurality of second individual electrodes 1332, 1342—along with a tissue attachment screw 1360. A defibrillator coil 1312 may be positioned close to the distal end of the flexible conduit 1310. The wire diameter and the location may be selected such that it may act as a mechanical stop to limit the deployment depth of the flexible conduit 1300 into the septum of the heart.

In further embodiments, the distal end of the conduit (whether it is equipped with the defibrillator coil 1312 or not) may terminate with a small distal enlargement 1380 sized to have an outside diameter greater than that of the flexible conduit 1310 so as to act more effectively as a mechanical stop during deployment of the flexible conduit 1300 of the invention.

Examples of a suitable design concepts for the defibrillator coil may be found in U.S. Pat. Nos. 7,236,828, 5,456,706, 5,772,689 incorporated herein by reference. In addition to serving as a mechanical stop, the defibrillator coil 1312 may be used for sensing electrical signals of the heart—both during the step of interrogation of individual electrodes as well as during the subsequent operation of the pacemaker. To operate the defibrillator coil 1312, the pacemaker controller may be equipped with additional cardioverter/defibrillator circuitry configured to apply a suitable shock upon meeting predetermined shock criterion that are used in implantable cardioverter-defibrillators.

A leadless ICD is also contemplated to be included in the scope of the present invention. in this case, a housing of such leadless device may be implanted in the right ventricle at the location of the intraventricular septum with multiple individual electrodes protruding therefrom as described elsewhere. The housing may also support a defibrillator coil supported outside thereof and positioned to be operably coupled to cardiac tissue of the subject.

In further embodiments, a flexible conduit comprising at least a plurality of first individual electrodes deployed in the left bundle branch as well as a defibrillator coil as described above may be further configured to operate together with at least one or more electrode deployed in a coronary sinus of the subject to be in operational contact with the left ventricle. This combination of intraseptal pacing electrodes, at least one or more coronary sinus pacing electrodes and a defibrillator coil may together create an alternative configuration suitable for acting as a cardiac resynchronization therapy (CRT) apparatus. This may be advantageous in a variety of specific arrhythmia conditions combined with heart failure such as for example in subjects where conduction abnormalities may originate further down the line of the left bundle branch conduction fibers.

Figure 17:
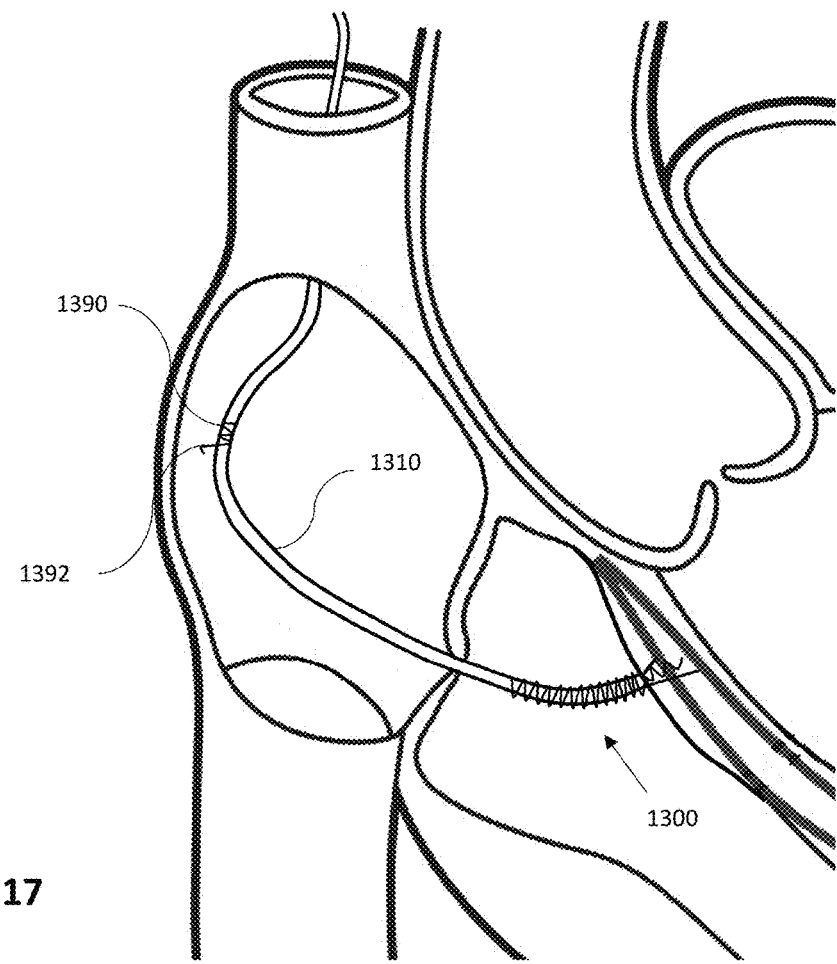
FIG. 17 shows one suitable implantation position of the device depicted in FIG. 16, further coupled with a supplemental atrial electrode.

FIG. 17 shows an example of one implantation approach for a device shown in FIG. 16. In this case, the distal end of a combination of a pacemaker and cardioverter/defibrillator 1300 is implanted at the interventricular septum of the heart. An optional atrial electrode 1392 may be provided as extending from a coil 1390 positioned along the flexible conduit 1310. During deployment, a delivery sheath (not shown is positioned to surround the flexible conduit 1310 so as the electrode wire 1392 is held next to the flexible conduit and does not extend outwards until released. Once the distal end of the device 1300 is deployed, the delivery sheath is moved back releasing the elastic wire of the electrode 1392 (such as Nitinol wire) so as to allow it to extend outwards and away from the flexible conduit 1310. Pulling or pushing on the flexible conduit 1310 may be used to cause the hook of the electrode 1392 to engage with the cardiac tissue of the right atrium whereby securing thereof to the heart of the subject.

Figure 18:
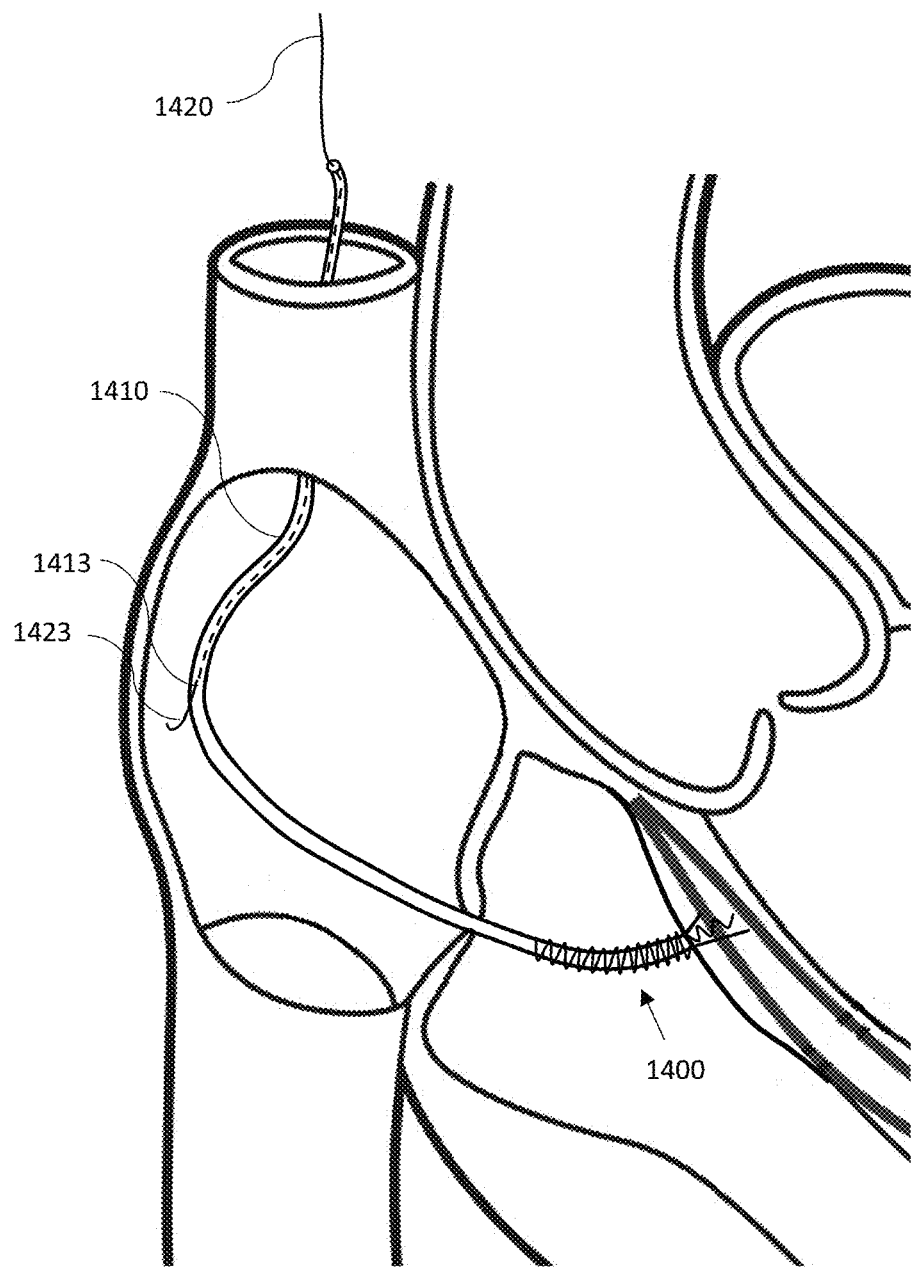
FIG. 18 shows the same but with an alternative design for the supplemental atrial electrode.

A further embodiment is shown during deployment stage in FIG. 18. Shown here is device 1400 with a distal end deployed at the interventricular septum of the heart such as using designs and approaches described above for one or several other embodiments of the present invention. The flexible conduit 1410 may have a side opening 1413 located proximally to the distal end thereof to correspond to a location inside the right atrium. A flexible individual electrical wire 1420 may be positioned inside the flexible conduit 1410 in a dedicated slot leading to the opening 1413. Once the distal end of the flexible conduit 1400 is deployed, the individual electrical wire 1420 may be operated to slide forward causing the individual atrial electrode 1423 to emerge from the opening 1413 and engage with the cardiac tissue of the atrium. The electrode 1423 may be shaped to have a hook at the end or another feature to allow it to securely remain inside the atrial tissue. For this purpose, the atrial electrode 1423 (as well as the individual electrical wire 1420) may be made from Nitinol to assure their flexibility and ability to assume a predetermined shape once outside the flexible conduit 1410.

Figure 19:
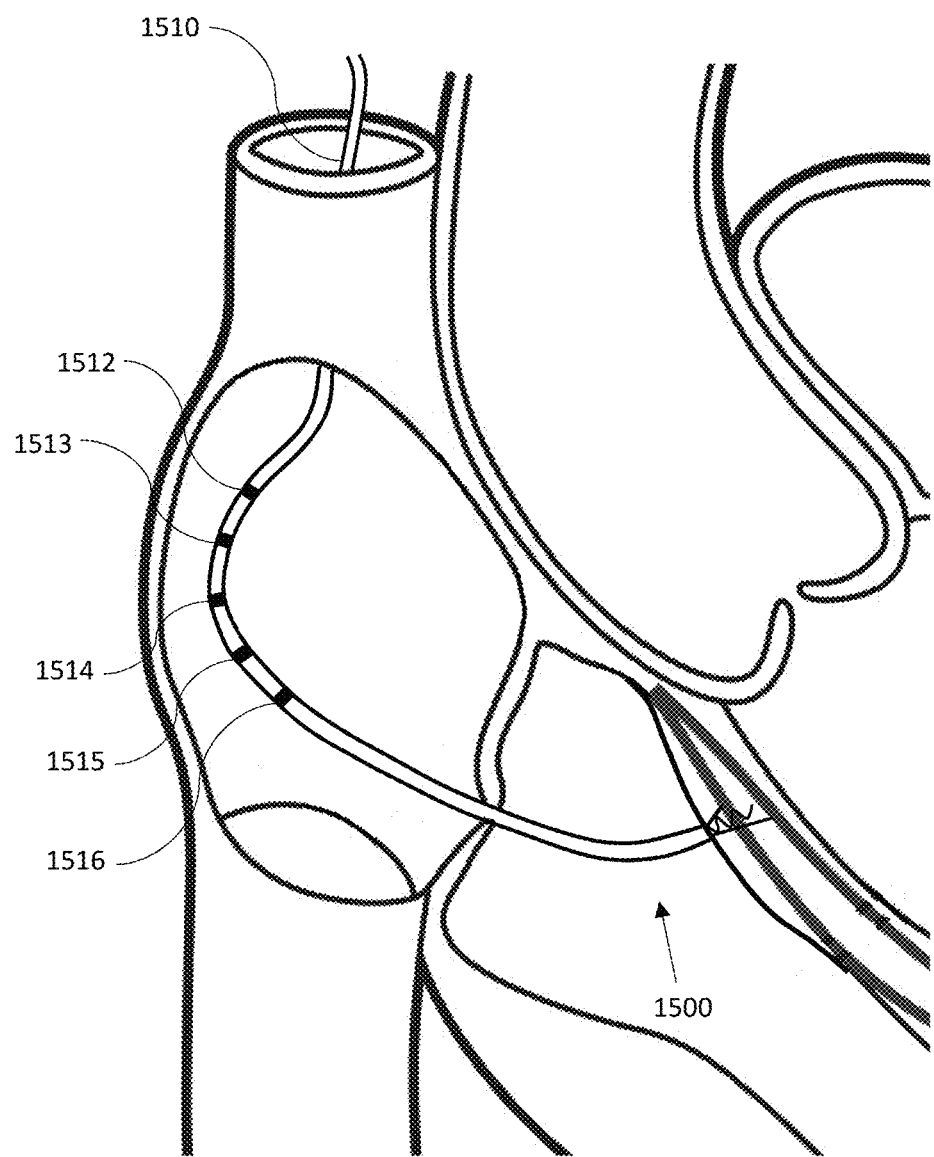
FIG. 19 shows the intraseptal multi-electrode cardiac pacemaker equipped with yet another embodiment of the supplemental atrial electrode, and finally

A further embodiment of the present invention is shown in FIG. 19, where the flexible conduit 1510 of the device 1500 contains a plurality of atrial individual electrodes 1512, 1513, 1514, 1515, and 1516. In embodiments, 1, 2, 3, 4, 5, 6, 7, 8, 9, 10, 11, 12, 13, 14, 15, 16 or more of atrial individual electrodes may be used. These electrodes may be formed as spaced apart rings on the flexible conduit 1510. The most distal atrial electrode 1516 may be spaced away from the distal end of the flexible conduit 1510 by about 40 to about 140 mm so as to assure positioning thereof in the right atrium of the heart. In embodiments, the most distal atrial electrode may be spaced away from the distal end of the flexible conduit 1510 by about 40, 50, 60, 70, 80, 90, 100, 110, 120, 130, 140 mm or any distance therebetween as the invention is not limited in this regard.

The spacing between individual atrial electrodes may be the same or variable between individual pairs of atrial electrodes. Such spacing may vary from about 5 mm to about 30 mm and may be about 5, 10, 15, 20, 25, 30 mm or any other distance inbetween as the invention is not limited in this regard.

Following deployment, an interrogation of a plurality of individual atrial electrodes may be conducted to select one or more atrial individual electrodes based on predetermined atrial acceptance criterion. In embodiments, such atrial acceptance criterion may be capture of the right atrium or sufficient sensing of the natural electrical signals generated by the heart. Secondary stratification of selected atrial electrodes may be conducted using an additional criterion such as the lowest voltage threshold of atrial capture.

Figure 20:
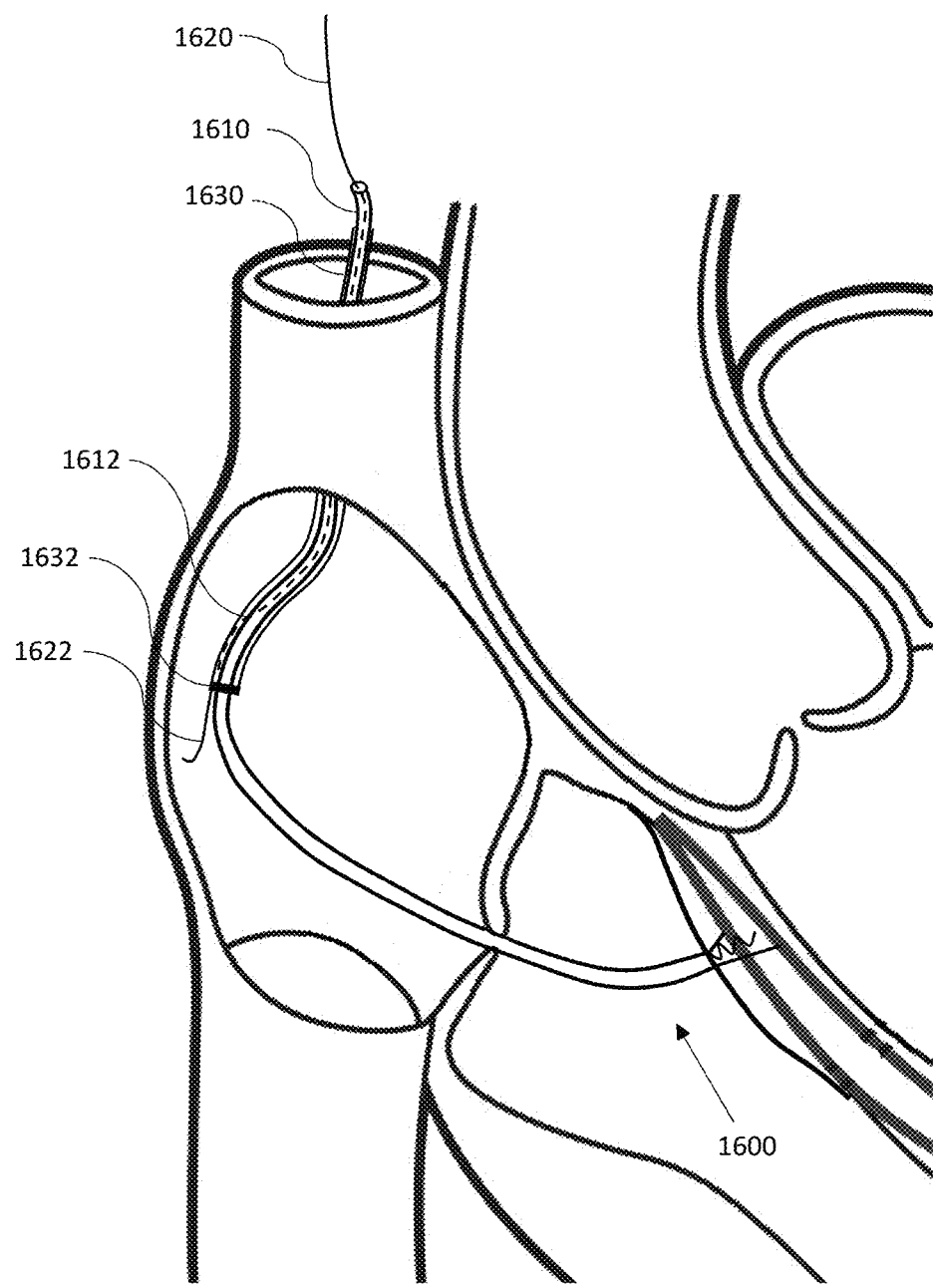
FIG. 20 is yet another embodiment similar to that shown in FIG. 19 but with yet a further variation of the supplemental atrial electrode.

A further yet embodiment 1600 of the present invention is shown in FIG. 20 which is configured to allow placement of the atrial individual electrode 1622 at any desired location along the flexible conduit 1610. To accomplish this, an individual electrode wire 1620 is slidably positioned inside an individual slot inside the flexible conduit 1610 terminating with a side opening 1612. The location of the side opening 1612 may be selected to be proximal to a desired range of implantation positions of the atrial electrode 1622 in the cardiac tissue of the right atrium. The delivery sheath 1630 may be used to first slidably position the distal end of the flexible conduit 1610 and secure thereof to the interventricular septum. The distal end of the delivery sheath 1630 may be equipped with a radiopaque marker such as a metal ring 1632 so that retraction of the delivery sheath 1630 after securement of the distal end of the flexible conduit 1610 may be monitored on a screen using X-Ray or fluoroscopy.

Once the flexible conduit 1610 is secured to the septum, the delivery sheath 1630 may be retracted to place the distal end thereof at a desired atrial location for placement of the atrial electrode 1622. The individual electrode wire 1620 may be moved forward to cause the atrial electrode 1622 to emerge from the side opening 1612, advance forward inbetween the delivery sheath 1630 and the flexible conduit 1610 and emerge at the distal end of the delivery sheath 1630. The atrial electrode 1622 may be pre-shaped to extend outwards so as to engage with the atrial tissue and secure itself at the desired position inside the right atrium of the heart. The delivery sheath 1630 may be then withdrawn entirely and the proximal end of the flexible conduit 1610 including the individual electrical wire 1620 may be connected to the pacemaker controller for operating the device to pace both the right atrium as well as one or both ventricles of the heart.

Once a plurality of first and/or second individual electrodes is placed inside the interventricular septum and connected to the pacemaker controller, a process of interrogation of individual electrodes may be performed. In embodiments, first individual electrodes may be assessed for meeting first redetermined criterion such as acceptable level of sensing of natural electrical signals and/or for acceptable capture of the left ventricle of the heart as was described in greater detail in my previous patent applications. Individual first electrodes meeting the first acceptance criterion may be selected for further activation, while those individual first electrodes that did not meet the predetermined first acceptance criterion may be abandoned. If more than one individual first electrode has been selected as acceptable, further stratification may be conducted using additional acceptance criterion, for example the first individual electrode with the lowest voltage of left ventricle myocardial capture via the left bundle branch may be preferred for using in subsequent pacing of the left ventricle.

A similar approach may be conducted for the plurality of second individual electrodes—selecting those second electrodes that meet a predetermined second acceptance criterion. One example of such second acceptance criterion is capture of the right ventricular myocardium via the right bundle branch, preferably at the lowest possible voltage. Other second individual electrodes may be abandoned.

While interrogation of pluralities of both first and second individual electrodes may be conducted independently, in some circumstances the actual pacing of the left ventricle may induce conduction abnormalities in the right ventricle. If this is the case, it may be advantageous to first interrogate the plurality of first individual electrodes, select a subset of those first individual electrodes suitable for delivering a pacing therapy to the heart, initiate such pacing therapy by capturing and pacing the left ventricle via the left bundle branch—and afterwards conduct interrogation of the plurality of the second individual electrodes while left ventricular pacing is ongoing. This approach may be useful to select one or more of the second individual electrodes as most suitable for right ventricular capture via the right bundle branch to correct possible anomalies that may be caused by pacing the left ventricle at the same time.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of providing intraseptal cardiac pacing comprising the steps of:
   a. providing a flexible conduit housing a plurality of first individual electrical wires extending therethrough and terminating with a corresponding plurality of first individual electrodes extending from a distal end of said flexible conduit,
   b. advancing said flexible conduit through a right atrium and into a right ventricle to position said distal end thereof at an interventricular septum,
   c. deploying said plurality of first individual electrodes at a predetermined first distance into said interventricular septum, said predetermined first distance is selected to cause said plurality of first individual electrodes to operably reach left bundle branch conduction fibers inside said interventricular septum, d. interrogating said plurality of first individual electrodes to determine a subset thereof meeting a first predetermined acceptance criterion, and e. initiating said intraseptal cardiac pacing using at least some of said first individual electrodes of said subset of first individual electrodes meeting said predetermined acceptance criterion, wherein said at least some first individual electrodes are connected to a cardiac pacemaker.

2. The method as in claim 1, wherein said first predetermined acceptance criterion in step (d) is capture of conduction system fibers located within said interventricular septum.

3. The method as in claim 2, wherein in step (e) said subset of first individual electrodes is further stratified based on a lowest voltage threshold necessary for achieving said capture of conduction system fibers located within said interventricular septum.

4. The method as in claim 1 further comprising a step (f) of leaving remaining first individual electrodes in a passive state implanted in said interventricular septum.

5. The method as in claim 1, wherein said step (f) further including a step of re-evaluating at least some of said first individual electrodes for meeting said first predetermined acceptance criterion and changing said subset of selected first individual electrodes when a malfunction of the previously selected first electrodes is detected.

6. The method as in claim 1, wherein in step (c) said plurality of first individual electrodes are deployed into said interventricular septum to operably reach said left bundle conduction fibers distally of a bifurcation of His Bundle conduction fibers into said left bundle branch conduction fibers and a right bundle branch conduction fibers.

7. The method as in claim 6, wherein in step (a) said flexible conduit further housing a plurality of second individual electrical wires extending therethrough and terminating with a corresponding plurality of second individual electrodes extending from a distal end of said flexible conduit, said step (c) further comprising deploying said plurality of second individual electrodes at a predetermined second distance into said interventricular septum, said predetermined second distance is selected to cause said plurality of second individual electrodes to operably reach said right bundle branch conduction fibers inside said interventricular septum.

8. The method as in claim 7, wherein step (d) further comprising interrogating said plurality of second individual electrodes to determine a subset thereof meeting a second predetermined acceptance criterion.

9. The method as in claim 6, wherein in step (a) said flexible conduit further comprises a defibrillator coil at said distal end thereof, said method further comprising a step of activating said defibrillator coil to apply a suitable shock upon meeting a predetermined shock criterion.

* * * * *